(12) United States Patent
Lancaster et al.

(10) Patent No.: US 7,711,579 B2
(45) Date of Patent: May 4, 2010

(54) SYSTEM AND METHOD FOR MANAGING DISCHARGE WORKLOAD IN HEALTHCARE ENVIRONMENT

(75) Inventors: Brian J. Lancaster, Shawnee, KS (US); Jill Hagel, Lenexa, KS (US)

(73) Assignee: Cerner Innovation, Inc., Overland Park, KS (US)

( * ) Notice: Subject to any disclaimer, the term of this patent is extended or adjusted under 35 U.S.C. 154(b) by 924 days.

(21) Appl. No.: 11/304,366

(22) Filed: Dec. 15, 2005

(65) Prior Publication Data

US 2007/0142713 A1    Jun. 21, 2007

(51) Int. Cl.
*G06Q 10/00* (2006.01)
*G06Q 50/00* (2006.01)

(52) U.S. Cl. .......................................... 705/2
(58) Field of Classification Search .................... 705/2, 705/4

See application file for complete search history.

(56) References Cited

U.S. PATENT DOCUMENTS

| | | | |
|---|---|---|---|
| 5,065,315 A * | 11/1991 | Garcia ........................... 705/2 |
| 5,809,477 A | 9/1998 | Pollack | |
| 5,995,937 A | 11/1999 | DeBusk et al. | |
| 6,061,657 A | 5/2000 | Whiting-O'Keefe | |
| 6,193,654 B1 | 2/2001 | Richardson et al. | |
| 6,314,556 B1 | 11/2001 | DeBusk et al. | |
| 7,076,436 B1 | 7/2006 | Ross, Jr. | |
| 7,155,399 B2 | 12/2006 | Andre et al. | |
| 2003/0050797 A1 | 3/2003 | Brandt et al. | |
| 2003/0101076 A1 | 5/2003 | Zaleski | |
| 2003/0220815 A1 | 11/2003 | Chang et al. | |
| 2005/0075902 A1 * | 4/2005 | Wager et al. .................... 705/2 |

* cited by examiner

*Primary Examiner*—Gerald J. O'Connor
*Assistant Examiner*—John A Pauls
(74) *Attorney, Agent, or Firm*—Shook Hardy & Bacon LLP (57) ABSTRACT

A computerized system and method for determining a discharge workload score for a patient and a discharge planner is provided. A first discharge data element for a patient is received and assigned a first value. A second discharge data element for the patient is received and assigned a second value to the second discharge data element. The first and second values are utilized to determine a discharge workload score for the patient. The one or more patients for a care planner are determined. The workload score for each of the one or more patients is accessed and the workload scores are utilized to determine an overall workload score for the care planner.

15 Claims, 5 Drawing Sheets

┌─ 602
| PATIENT NAME: JOHN DOE        DOB: 2/22/68
| ID: 001
604 — DISCHARGE PLANNER: JANE JACKSON
606 — DISCHARGE LOCATION [     ]
608 — DISCHARGE WITH DME [     ]
610 — DISCHARGE WITH TRANSPORTATION [     ]
612 — EDUCATION PROVIDED [     ]
614 — TIME SPENT [     ]
616 — OTHER [     ]

| MANAGEMENT VIEW | | |
|---|---|---|
| DISCHARGE PLANNER | SCORE | TIME SPENT |
| JANE DOE | | |
| 001 | 10 | 2 HOURS |
| 002 | 12 | 1.5 HOURS |
| 003 | 6 | 0.5 HOURS |
| TOTAL | 28 | 4 HOURS |
| JOHN JACKSON | | |
| 004 | 6 | 1.0 |
| 005 | 5 | 0.5 |
| 006 | 3 | 0.5 |
| TOTAL | 14 | 2 HOURS |

FIG. 7.

SYSTEM AND METHOD FOR MANAGING DISCHARGE WORKLOAD IN HEALTHCARE ENVIRONMENT

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND

When a patient is discharged from a healthcare facility a case manager or discharge planner assists the patient with discharge activities. These discharge activities may include assessing a patient's support system, reviewing patient data, verifying benefit plans, obtaining and managing referrals, coordinating activities, providing education, managing a discharge plan of care, discharging the patient to different locations and with durable medical equipment and transportation. Some patient discharge plans are simple while others are complex and take a great deal of time to implement.

Currently, it is difficult to balance the workload of discharge case managers within a healthcare facility. Current systems do not determine the complexity of discharge plans for each patient and only look to the number of cases being handled by a case manager. Current systems also do not provide any method for tracking case managers who are dealing with complex-discharge plans and those who are dealing with less complex discharge plans. Thus, some case managers create multiple complex discharge plans for patients while others are dealing with simpler discharge plans.

SUMMARY

In one embodiment, a method in a computerized environment for determining a discharge workload score for a patient is provided. A first discharge data element for a patient is received and assigned a first value. A second discharge data element for the patient is received and assigned a second value to the second discharge data element. The first and second values are utilized to determine a discharge workload score for the patient.

In another embodiment, a method in a computerized environment for determining a workload score for a care planner in a healthcare environment is provided. One or more patients for a care planner are determined. The workload score for each of the one or more patients is accessed. The workload score for each of the one or more patients is utilized to determine an overall workload score for the care planner.

In still another embodiment, a computerized method for displaying workload scores for multiple discharge planners in a healthcare environment is shown. A request is received to display workload scores for one or more discharge planners. An overall workload score for the one or more discharge planners is accessed. The overall workload scores for the one or more discharge planners are displayed.

BRIEF DESCRIPTION OF THE SEVERAL VIEWS OF THE DRAWINGS

The present invention is described in detail below with reference to the attached drawing figures, wherein.

DETAILED DESCRIPTION

Embodiments of the present invention are directed to a system and method for managing discharge workload in a healthcare environment.

Having briefly provided an overview of the present invention, embodiments of the invention will be discussed with reference to FIGS. 1-7.

Figure 1:
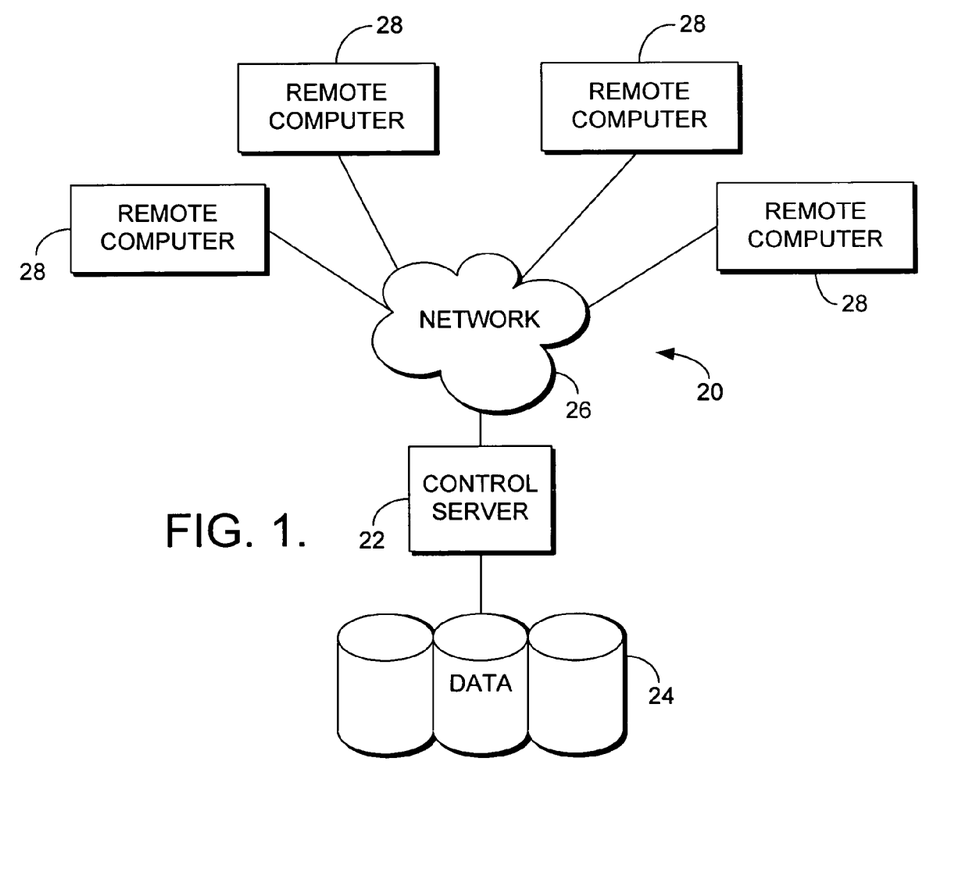
FIG. 1 is a block diagram of an operating environment for use with an embodiment of the present invention.

With reference to FIG. 1, an exemplary medical information system for implementing embodiments of the invention includes a general purpose-computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical or research environment, for example, but not limited to, clinical laboratories, hospitals, other inpatient settings, a clinician's office, ambulatory settings, medical billing and financial offices, hospital administration, veterinary environment and home health care environment. Clinicians include, but are not limited to, the treating physician, specialists such as surgeons, radiologists and cardiologists, emergency medical technologists, discharge planners, care planners, physician's assistants, nurse practitioners, nurses, nurse's aides, pharmacists, dieticians, microbiologists, laboratory experts, laboratory scientist, laboratory technologists, genetic counselors, researchers, veterinarians and the like. The remote computers may also be physically located in non-traditional medical care environments so that the entire health care community is capable of integration on the network. Remote computers 28 may be a personal computer, server, router, a network PC, a peer device, other common network node or the like, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention. Although the method and system are described as being implemented in a LAN operating system, one skilled in the art would recognize that the method and system can be implemented in any system.

Figure 2:
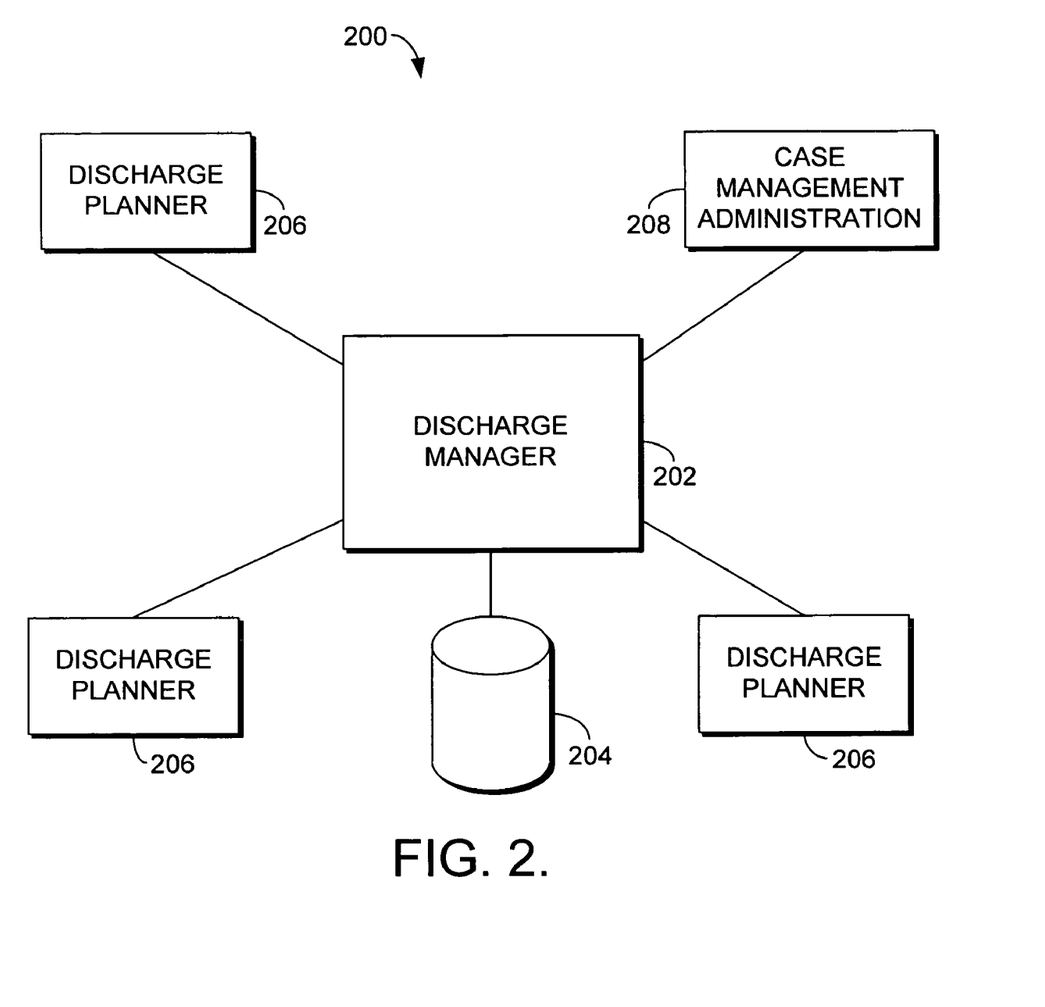
FIG. 2 is a flow diagram illustrating the documentation of discharge activity by a case manager in accordance with an embodiment of the present invention.

With reference to FIG. 2, a block diagram is provided illustrating an exemplary architecture 200 for facilitating discharge workload management in accordance with an embodiment of the present invention. As shown in FIG. 2, a discharge manager 202, may be provided to collect, coordinate and utilize discharge data for patients. Discharge data and other information may be maintained in an associated computerized database 204. Association of a discharge planner and a patient may also be maintained in associated computerized database 204 or may be maintained in a separate computerized database. In one embodiment, the associated computerized database comprises electronic medical records for patients.

In operation, as shown in FIG. 2, the discharge manager 202 is capable of receiving discharge data for multiple patients from multiple discharge planners 206. Discharge planners assist patients with discharge activities and prepare them to be discharged from a healthcare facility, such as a hospital. These discharge activities may include assessing a patient's support system, reviewing patient data, verifying benefit plans, obtaining and managing referrals, coordinating activities, providing education, managing a discharge plan of care, discharging the patient to different locations and with durable medical equipment and transportation. Documentation of discharge activities, along with assessments of the patient, location patient is discharged to, condition of patient at discharge, transportation for patient being discharged and the amount of time spent by a discharge planner to discharge a patient are types of discharge data received from discharge planners 206.

The discharge data received from the discharge planners 206 is utilized by a rules engine of the discharge manager 202 to calculate the workload or social acuity score for one or more patients and one or more discharge planners. The rules engine assigns values or weights to the discharge data received. The rules engine may also assign a value or weight to the amount of time a patient has been hospitalized or the amount of time a caregiver spends on discharging a patient. The amount of time a discharge planner spends on discharging a patient may be measured in a variety of ways including, a time documented by the discharge planner or the amount of time the discharge planner spends documenting discharge activities for the patient in the system. Table 1, shown below, includes exemplary weighted values assigned to exemplary discharge activities. After a workload or social acuity score has been assigned a patient and/or discharge planner, the score may be displayed to case management administration 208.

The discharge manager 202 is capable of communicating with multiple discharge planners 206, case management administration 208 and the patient's electronic medical record which may be maintained in associated database 204. In an alternative embodiment, the discharge data input by the one or more discharge planners 206 is first populated into a patient's electronic medical record. The discharge data is then accessed by the discharge manager 202 and utilized to calculate the workload for one or more of the multiple discharge planners 206. The workload calculations are communicated from the discharge manager 202 to case management administration 208.

Each discharge planner 206 and case management administration 208 may have a computing device, such as a remote computer 28 of FIG. 1, for communicating with discharge manager 202 and the various entities via one or more networks, which may comprises one or more wide area networks (WANs) and one or more local area networks (LANs) as well as one or more public networks, such as the Internet, and one or more private networks. In some embodiments, the discharge planners 206 and case management administration 208 may have a native clinical computing system, such as the CERNER MILLENNIUM system provided by Cerner Corporation of Kansas City, Mo., in which to communicate with the discharge manager 202.

Figure 3:
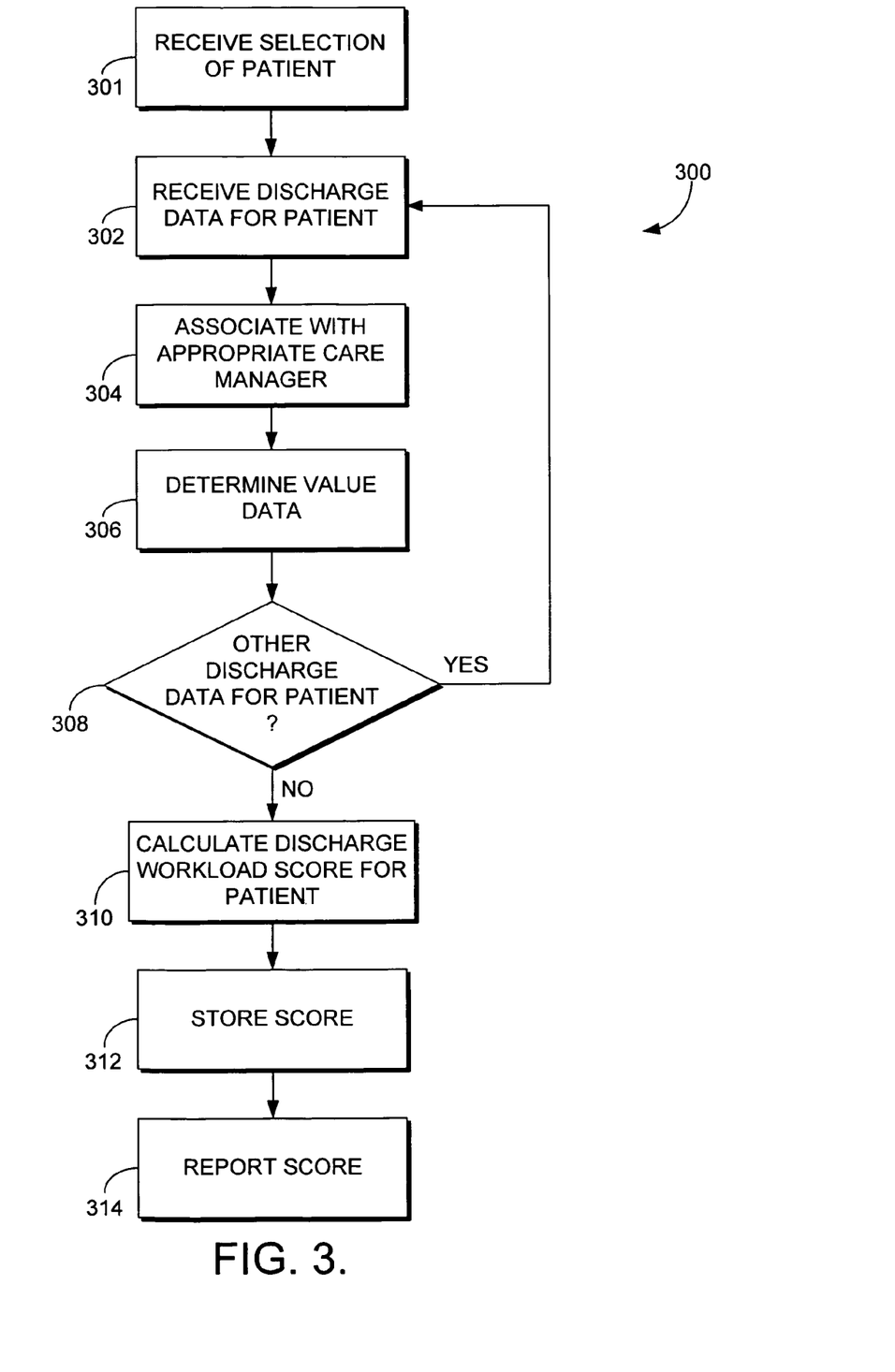
FIG. 3 is a flow diagram illustrating a method for calculating and reporting a workload score for a patient in accordance with an embodiment of the present invention.

With reference to FIG. 3, a method 300 for receiving discharge activity data for a patient is shown. At step 301, the selection of the patient for whom documentation of discharge activities is received. For example, a discharge planner assigned to the patient may have a work list comprising patients for whom he or she is responsible for preparing to be discharged. The discharge planner selects the patient from the work list for whom he or she is documenting discharge activities. At step 302, the discharge activity for the patient is received.

Figure 6:
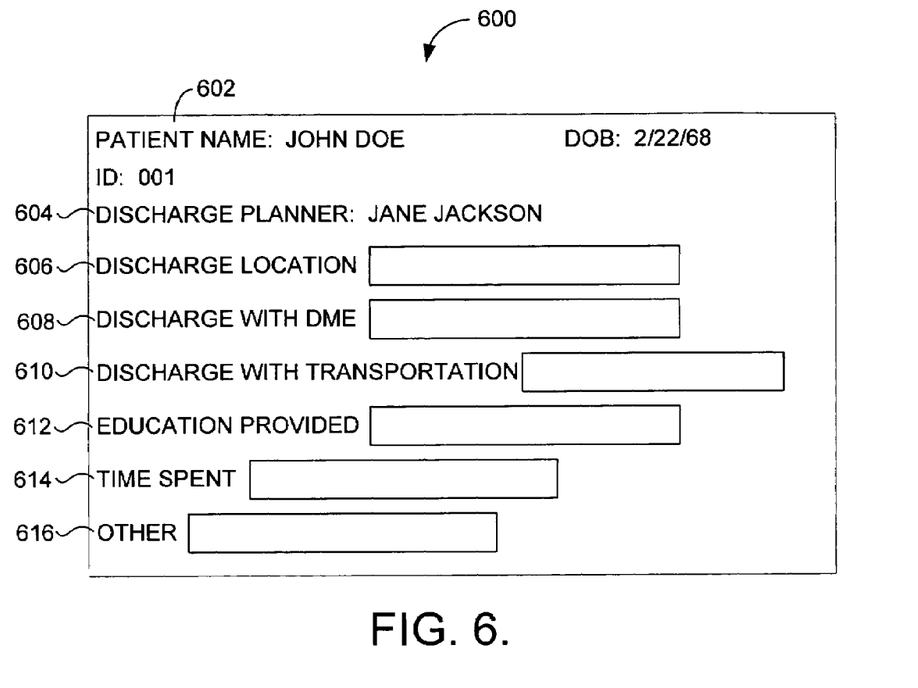
FIG. 6 is an exemplary screen for the input of discharge data for a patient in accordance with an embodiment of the present invention.

In operation, a discharge planner inputs the discharge data for the patient. For example, after reviewing the patient's case, the discharge planner determines the appropriate discharge activities needed for the patient and accesses the patient's discharge condition and discharge needs. With reference to FIG. 6, an exemplary discharge documentation form 600 is shown. Discharge location 606, discharge with durable medical equipment 608, discharge with transportation 610, patient education provided 612, time spent on discharge activities by the discharge planner 614 and other discharge information 616 may be documented on discharge documentation form 600 for an identified patient 602 (John Doe) by the identified discharge planner 604 (Jane Jackson).

Exemplary discharge documentation form 600 allows for free text of discharge data to be entered for the identified patient 602. However, in an alternative embodiment, interactive drop down menus may be provided for the discharge location, discharge with durable medical equipment, discharge with transportation, education provided and time spent documenting activities providing the user with options for documenting discharge data. For example, discharge location may include to patient's home, acute care facility, extended care facility, skilled nursing facility, rehabilitation and hospice. References to possible nearby discharge locations may also be included as options for the user. From documentation form 600, additional forms and options may be provided and accessed for the documentation of discharge data.

Possible discharge activities include assessing the patient's support system, reviewing patient data, verifying a patient's benefit plan, managing patient referrals, coordinating activities, providing education to the patient, sending notification, managing the discharge plan of care, and managing discharge orders for the patient. Assessment of the patient's discharge condition include analyzing the overall health condition of the patient, location of the patient being discharged to (e.g. home alone or skilled nursing facility), and the identification transportation and durable medical equipment needed for the patient.

The discharge data received helps assess the complexity of a patient's discharge case. For example, a patient requiring discharge to an extended care facility by ambulance with oxygen and a wheelchair is a more complex discharge case than a patient discharged to her own home with a spouse without any durable medical equipment or need for transportation. The discharge planner handling the patient being discharged to an extended care facility will have to spend more time discharging the patient being discharged to her own home.

Referring again to FIG. 3, at step 304, the system associates the patient with the appropriate care manager or discharge planner if the association has not already been made in the patient's electronic medical record or elsewhere. At step 306, the value or weight for the discharge data received is determined. The value may be determined by accessing a table or database having the appropriate score for the discharge data such as exemplary Table 1, shown below.

TABLE 1

| Discharge Data Values | |
|---|---|
| Discharged to home: | |
| Alone | 3 |
| With spouse | 2 |
| With family | 2 |
| With friend | 2 |
| With sitter | 3 |
| With parents | 1 |
| With grandparents | 2 |
| Own home | 1 |
| Family's home | 2 |
| Foster home | 2 |
| Friend's home | 2 |
| Other: | |
| Discharged to another Acute Care Facility | 4 |
| Discharged to Extended Care Facility | 5 |
| Discharged to Skilled Nursing Facility | 6 |
| Discharged to Rehab | 5 |
| Discharged with Hospice | 4 |
| Discharged with Home Health | 5 |
| Discharged with home IV Therapy | 5 |
| Discharge with Durable Medical Equipment | |
| Apnea monitor | 4 |
| Bedside commode | 1 |
| Cane | 2 |
| Trach/bipap/cpap/resp medical equip | 4 |
| CPM machine | 2 |
| Crutches | 1 |
| Feeding pump | 3 |
| Hospital bed | 2 |
| Hoyer lift | 2 |
| IV pump/supplies | 3 |
| Nebulizer | 3 |
| Oxygen | 2 |
| Shower chair | 1 |
| Suction equipment | 2 |
| Traction | 2 |
| Walker | 1 |
| Wheelchair | 2 |
| Other: | |
| Discharged with transportation | |
| Air ambulance | 5 |
| Ambulance | 3 |
| Bus tickets | 1 |
| Taxi (CM dept) | 2 |
| Taxi (self) | 1 |
| Family | 0 |
| Friend | 0 |
| Medicaid van | 2 |
| Police | 1 |
| Wheelchair van | 2 |

By way of example, if the patient is being discharged to an extended care facility, the discharge data for such would receive a value of 5 points and that would be added to the patient's overall workload or acuity score.

At step 308, it is determined whether there are any additional discharge data for the patient to be documented. If there are additional discharge data documented for the patient, the system returns to step 302 to receive this discharge data. If at step 308 it is determined that there are no additional discharge activities for the patient to be documented, at step 310, the workload or social acuity score is calculated for the patient.

In one instance this may be done by summing the total of the values or weights assigned to documented discharge data for the patient. In alternative embodiments, algorithms or other mathematical calculations may also be utilized. At step 312, the calculated workload or social acuity score is stored. In one embodiment, the calculated workload score may be stored in the patient's electronic medical record. At step 314, the score is reported to management so that workload may be balanced accordingly.

Figure 4:
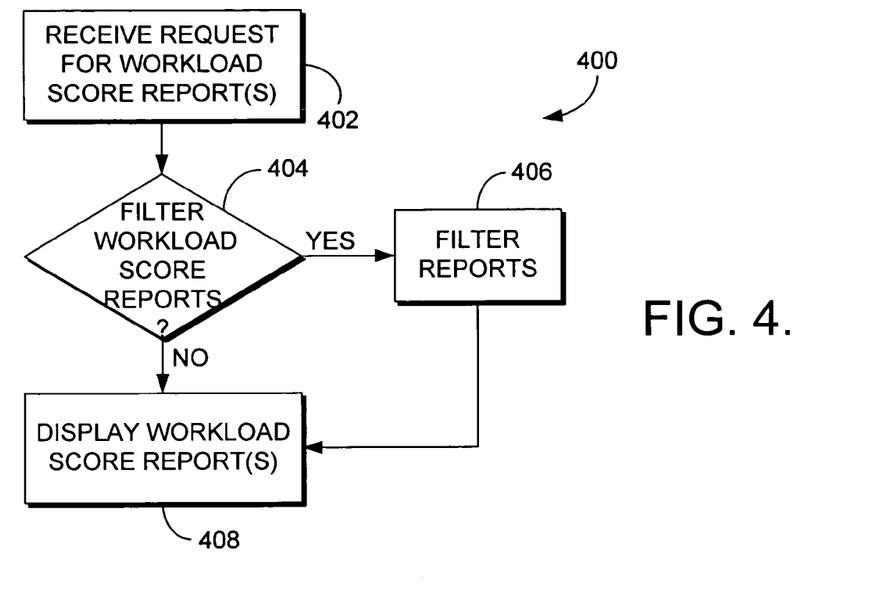
FIG. 4 is a flow diagram illustrating a method for filtering activity score reports for display in accordance with an embodiment of the present invention.

With reference to FIG. 4, a method 400 for displaying activity score reports is shown. At step 402, a request to view workload score reports for discharge planners is received. For example, a case management administrator may request to view workload reports for discharge planners at a healthcare facility. At step 404, it is determined whether the workload reports are to be filtered. By way of example, and not by limitation, a case management administrator may request to view workload reports for specific discharge planners, locations or based on workload scores. The filter criteria may include location, identity of discharge planner(s), and workload score. If the workload reports are to be filtered based on particular criteria at step 406, the reports are filtered accordingly, and the filtered workload reports are displayed at step 408. If at step 404 the workload reports are not to be filtered, workload scores for all discharge planners for the healthcare facility are displayed.

Figure 5:
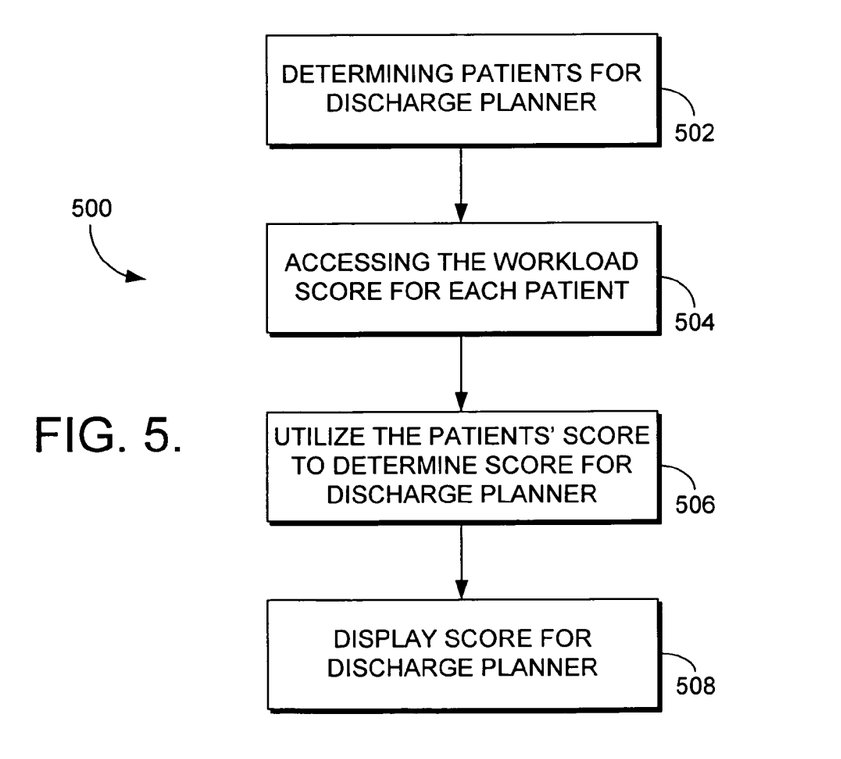
FIG. 5 is a flow diagram illustrating a method for determining a workload score for a discharge planner in accordance with an embodiment of the present invention.

Referring next to FIG. 5, a method 500 for determining a workload score for a discharge planner is shown. At step 502, the patients for whom the discharge planner has been assigned are determined. This may be done by accessing a work list for the discharge planner and/or electronic medical records for the patient. In one embodiment, the workload score for the discharge planner is determined by the patients for which the discharge planner is currently responsible. At step 504, the workload score for each patient is accessed. The workload score for each patient may be calculated and stored as described in FIG. 3.

At step 506, the workload score accessed for each patient of the discharge planner is utilized to determine the workload score for the discharge planner. In one embodiment, the workload scores for the patients are added to calculate the total workload score for the discharge planner. In alternative embodiments, other algorithms and mathematical equations may also be utilized. At step 508, the total workload score for the discharge planner is displayed or communicated to the proper administrator.

Figure 7:
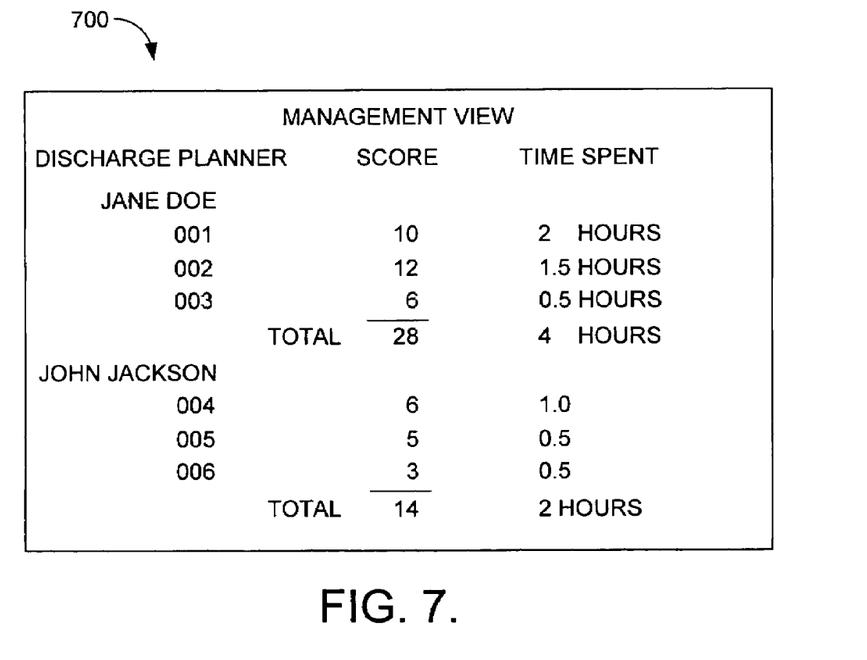
FIG. 7 is an exemplary screen displaying the discharge workload for case managers at a healthcare facility in accordance with an embodiment of the present invention.

With reference to FIG. 7, an exemplary workload score report 700 is shown. The workload score report 700 includes workload information for two discharge planners. As reported, discharge planner Jane Doe is responsible for three patients, identified by patient ID numbers. The workload score for each patient is displayed and the time that discharge planner Jane Doe has spent documenting discharge data for each patient is also displayed. The total workload score for all three of discharge planner Jane Doe's patients is 28 and her total time spent documenting discharge data is four hours.

Discharge planner John Jackson is also responsible for discharging three patients. However, the total workload score for all three of discharge planner John Jackson's patients is 14 and he has spent two hours documenting discharge data for his patients.

From report 700, a case management administrator can easily see that discharge planner Jane Doe is dealing with much more complex discharge cases than discharge planner John Jackson, even though discharge planner Jane Doe and John Jackson have the same number of patients to discharge. As such, to manage workload appropriately, if a new patient is ready for discharge, the case management administrator would assign the patient to John Jackson, rather than Jane Doe, based on the workload report 700.

In an alternative embodiment, the time spent documenting or completing discharge activities for a patient is assigned a value or weight and is added into the patient's workload score instead of being displayed simultaneously with the workload score as shown in FIG. 7.

The greater the total score and the time that the user spends documenting discharge data, the higher the social acuity levels of the patients being discharged. Thus, a case management administrator can track each discharge planner's activity and compare caseloads. This will promote optimal workload distribution among discharge planners and improve resource utilization and planning.

The present invention has been described in relation to particular embodiments, which are intended in all respects to illustrate rather than restrict. Alternative embodiments will become apparent to those skilled in the art that do not depart from its scope. Many alternative embodiments exist, but are not included because of the nature of this invention. A skilled programmer may develop alternative means for implementing the aforementioned improvements without departing from the scope of the present invention.

It will be understood that certain features and sub-combinations of utility may be employed without reference to features and sub-combinations and are contemplated within the scope of the claims. Furthermore, the steps performed need not be performed in the order described.

The invention claimed is:

1. A computer-implemented method, which utilizes a computing device having a server, a processor, and a computer storage medium, for determining a discharge-workload score of a patient, the method comprising:

receiving a first indication that the patient will be discharged with parents to a home of the patient;

responsive to receiving the first indication, retrieving from a database a first value that has been assigned to tasks required to discharge the patient with parents to the home of the patient, wherein when the patient is discharged with parents to the home, the first value is lower than when the patient is discharged without parents to the home;

receiving a second indication that the patient will be discharged with crutches;

responsive to receiving the second indication, retrieving from the database a second value that has been assigned to tasks required to discharge the patient with crutches, wherein when the patient is discharged with crutches the second value is lower than when the patient is discharged with a wheelchair;

receiving a third indication that the patient will be discharged with transportation provided by a family member;

responsive to receiving the third indication, retrieving from the database a third value that has been assigned to tasks required to discharge the patient with transportation provided by a family member, wherein when the patient is discharged with transportation that is provided by a family member, the third value is lower than when the patient is discharged with transportation provided by an non-family-member entity; and utilizing by the computing device the first, second, and third values to determine a discharge workload score of the patient.

2. The method of claim 1, wherein determining a discharge workload score for the patient comprises summing the first and second values.

3. The method of claim 1, further comprising:
receiving a third discharge data element for a patient; and
assigning a third value to the third data element.

4. The method of claim 3, further comprising:
utilizing the first, second and third values to determine a discharge workload score for the patient.

5. The method of claim 1, wherein the workload score for the patient is stored in the patient's electronic medical record.

6. The method of claim 1, further comprising:
utilizing all values for discharge data elements for the patient to determine the workload score for the patient.

7. One or more computer storage media having stored thereon computer-readable instructions that, when executed, enable a computing device to perform a method for determining a discharge-workload score of a patient, the method comprising:
receiving a first indication that the patient will be discharged by air ambulance;
responsive to receiving the first indication, retrieving from a database a first value that has been assigned to tasks required to discharge the patient by air ambulance, wherein when the patient is discharged with transportation by air ambulance, the first value is higher than when the patient is discharged with transportation that is not by air ambulance;
receiving a second indication that the patient will be discharged alone;
responsive to receiving the second indication, retrieving from the database a second value that has been assigned to tasks required to discharge the patient alone, wherein when the patient is discharged alone, the second value is higher than when the patient is discharged with a family member;
receiving a third indication that the patient will be discharged with an IV pump;
responsive to receiving the third indication, retrieving from the database a third value that has been assigned to tasks required to discharge the patient with the IV pump, wherein when the patient is discharged with the IV pump the third value is higher than when the patient is discharged with an oxygen supply; and
utilizing by the computing device the first, second, and third values to determine a discharge workload score of the patient.

8. The one or more computer storage media of claim 7, further comprising:
displaying the overall workload score for the care planner.

9. The one or more computer storage media of claim 8, further comprising:
determining the total time spent by the care planner documenting discharge data for the one or more patient's of the care planner.

10. The one or more computer storage media of claim 9, further comprising:
displaying the total time spent by the care planner documenting discharge data.

11. The one or more computer storage media of claim 7, further comprising:
determining one or more patients for a second care planner;
accessing the workload score for each of the one or more patients of the second care planner;
utilizing the workload score for each of the one or more patients of the second care planner to determine an overall workload score for the second care planner; and
displaying the overall workload score calculated for both of the care planners.

12. The one or more computer storage media of claim 7, wherein the workload scores for each of the one or more patients of the care planner are accessed from the electronic medical records of the patients.

13. One or more computer storage media having stored thereon computer-readable instructions that, when executed, enable a computing device to perform a method for determining a discharge-workload score of a patient, the method comprising:
receiving a first indication that the patient will be discharged to home with home IV therapy;
responsive to receiving the first indication, retrieving from a database a first value that has been assigned to tasks required to discharge the patient to home with home IV therapy;
receiving a second indication that the patient will be discharged with an IV pump and supplies;
responsive to receiving the second indication, retrieving from the database a second value that has been assigned to tasks required to discharge the patient with the IV pump and supplies, wherein when the patient is discharged with the IV pump and supplies, the second value is lower than when the patient is discharged with an apnea monitor;
receiving a third indication that the patient will be discharged in a wheelchair van;
responsive to receiving the third indication, retrieving from the database a third value that has been assigned to tasks required to discharge the patient in a wheelchair van, wherein when the patient is discharged in a wheelchair van the third value is lower than when the patient is discharged in an ambulance; and
utilizing by the computing device the first, second, and third values to determine a discharge workload score of the patient.

14. The one or more computer storage media of claim 13, further comprising:
displaying an overall workload scores for all discharge planners.

15. The one or more computer storage media of claim 14, further comprising:
displaying the overall workload scores for specified discharge planners.

* * * * *